United States Patent [19]

Mattock et al.

[11] Patent Number: 4,465,574

[45] Date of Patent: Aug. 14, 1984

[54] BLOOD FRACTIONATION IMPROVEMENT

[75] Inventors: Patrick Mattock, Oxford; Gordan F. Aitchison, Abingdon, both of England

[73] Assignee: United Kingdom Atomic Energy Authority, London, England

[21] Appl. No.: 362,662

[22] Filed: Mar. 29, 1982

[30] Foreign Application Priority Data

Apr. 8, 1981 [GB] United Kingdom ................ 8111056

[51] Int. Cl.³ .................. B01D 57/02; C25B 7/00; A61K 39/00
[52] U.S. Cl. ................... 204/180 R; 424/88; 424/101
[58] Field of Search .......... 204/180 R, 299 R, 300 R; 424/11, 88, 101; 260/112 R

[56] References Cited

U.S. PATENT DOCUMENTS 3,616,453 10/1971 Philpot .............................. 204/299
3,844,926 10/1974 Smyth et al. ..................... 204/300 X
4,149,957 4/1979 Gibson et al. ..................... 204/301
4,246,085 1/1981 Mattock .......................... 204/180 R
4,250,008 2/1981 Mattock .......................... 204/180 R

OTHER PUBLICATIONS

Chem. Abstracts, vol. 88, Nov. 10, 1977, 55060s.
Chem. Abstracts, vol. 94, Nov. 6, 1980, 36335t.
Chem. Abstracts, vol. 52, No. 21, 11-10-58, Col. 18751(g).
Chem. Abstracts, vol. 54, No. 1, 1-10-60, Col. 672(b).

Primary Examiner—T. M. Tufariello
Assistant Examiner—T. Williams
Attorney, Agent, or Firm—Larson and Taylor

[57] ABSTRACT

The extraction of Factor VIII, the antihaemophilic factor in blood, is difficult due to its instability and the presence of impurities. An initial Factor VIII containing aqueous solution such as blood plasma is purified by subjecting a Factor VIII containing aqueous migrant solution to continuous flow electrophoresis wherein flow takes place in an annular separation chamber and is stabilized by means of an angular velocity gradient; and collecting a separated Factor VIII component.

In order to separate the Factor VIII from albumin and firbrinogen, while obtaining good recoveries of Factor VIII (e.g. ~60%), the migrant solution is prepared by precipitating Factor VIII from the initial solution using ethanol, and removing and redissolving the precipitate in an aqueous medium and adjusting the pH to be within the range of 7.5 to 8.6, preferably 8.3 to 8.6.

3 Claims, 1 Drawing Figure

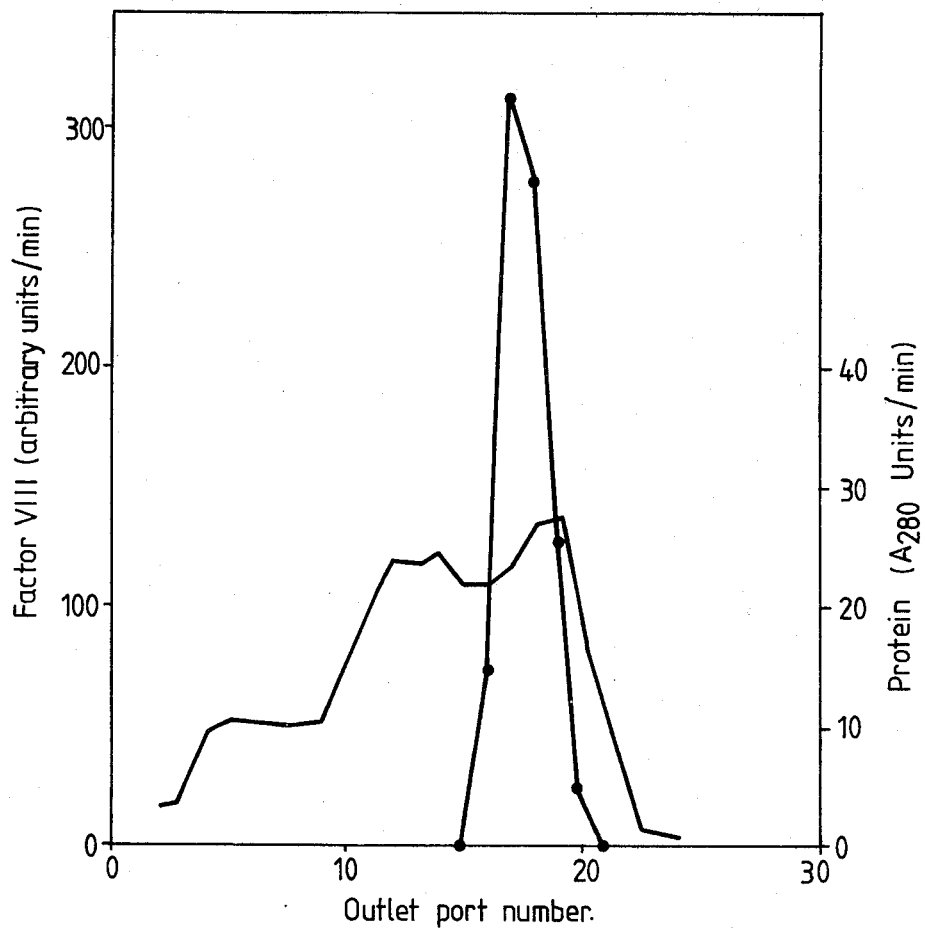

BLOOD FRACTIONATION IMPROVEMENT

The invention relates to a method of purifying a Factor VIII containing aqueous solution, such as blood plasma; continuous flow electrophoresis is used in a multi stage method to purify a Factor VIII containing solution, particularly from fibrinogen and albumin.

Factor VIII is the antihaemophilic factor in blood and there is much interest in its extraction, e.g. from blood plasma, so that it can be used in the treatment of patients suffering from haemophilia. It is, however, unstable and this has created difficulties in its extraction. Cryoprecipitation is a known method of extracting Factor VIII from blood plasma but has the disadvantage of poor recovery of Factor VIII from the initial plasma (e.g. about 40%) and of giving rise to a relatively dilute product which accordingly creates problems of administration to the patient because of the large volume of product required to a achieve a suitable dose level.

Another method of extracting Factor VIII from blood plasma is described in UK Patent Application Publication No. 2 023 662A (corresponding to U.S. Pat. No. 4,250,008) and makes use of continuous flow electrophoresis to separate Factor VIII from a Factor VIII containing solution of pH between 6 and 9. This method gives improved recoveries of Factor VIII compared with cryoprecipitation (e.g. at least 60%) and gives rise to a product containing virtually no fibrinogen and whose major contaminant is albumin.

The invention as claimed is a modification of the above-mentioned continuous flow electrophoretic separation process and is intended to meet the abovementioned problem of albumin contamination by removing albumin in a preliminary step before carrying out electrophoresis, without deleterious effect on the percentage recovery of Factor VIII.

Thus, the present invention provides a method of purifying an initial Factor VIII containing aqueous solution which comprises as steps of:

(i) contacting the initial solution with an organic liquid thereby to precipitate Factor VIII;
(ii) removing and redissolving the precipitate in an aqueous medium and adjusting the pH to be within the range of 7.5 to 8.6;
(iii) subjecting the product of step (ii) to continuous flow electrophoresis by injecting the solution as a migrant solution into a second aqueous solution, laminarly flowing in an annular separation chamber as a carrier solution for the migrant solution and stabilised by means of an angular velocity gradient, and applying a constant electric field across the resulting mixture to produce a differential movement of the Factor VIII component of the migrant solution with respect to the other major components of the solution perpendicular to the direction of flow of the layer; and
(iv) collecting the separated Factor VIII component.

It has been found that, in step (i), a significant proportion of the albumin contained in the initial Factor VIII containing solution when in the form of blood plasma is retained in the supernatant liquid. Thus, albumin can be removed from the Factor VIII and if required, can be recovered by methods known in the art. The albumin cannot then interfere with step (iii) above.

A further advantage of the method of the invention arises from the possibility of being able to redissolve the Factor VIII precipitate, in step (ii), in a smaller volume of aqueous medium than the volume of the initial solution, e.g. 0.6 of the volume of the initial solution. Because the initial solution, if in the form of blood plasma, would have to be diluted by a factor of 1.5 before being electrophoresed, an approximately three-fold increase in throughput in step (iii) can be achieved in comparison with the known electrophoresis method.

It has also been found that a high level of Factor VIII activity is present in the product of step (ii), e.g. about 85% of that present in the initial solution.

A further advantage of the method of the invention is that the product of step (ii) may be directly suitable for use in carrying out step (iii), i.e. there may be no necessity to reduce ionic strength as there is with blood plasma itself. Reduction of ionic strength is usually carried out by dialysis, a process which is not totally feasible on a large scale.

The organic liquid used in step (i) is preferably a water-miscible organic liquid and is most conveniently an alcohol such as ethanol which may for example constitute 25% (volume: volume) of the total liquid in step (i).

Where the initial solution is blood plasma, the product of step (ii) is found to contain other components such as immunoglobulins, fibrinogen and lipids. Factor VIII may, however, be separated from the immunoglobulins and fibrinogen in step (iii) as will be illustrated hereinafter. It has been found, that approximately 60% of the Factor VIII activity of the initial solution is recovered by the method of the invention.

Step (iii) is most conveniently carried out as generally described in UK Patent Specification No. 1 186 184 (corresponding to U.S. Pat. No. 3,616,453), which describes a process and apparatus where stabilisation of flowing streams in continuous flow electrophoresis is effected by an angular velocity gradient. Thus, the fractionation may be effected in an annular separation chamber defined between a central stationary cylinder (a stator) and an outer rotating cylinder (a rotor), which results in a gradient of angular velocity across the annular chamber giving laminar flow at high throughputs. The constant electric field is then applied across the annular chamber to produce the differential movement of the Factor VIII component of the migrant solution. Improvements and/or modifications of the apparatus described in UK Patent Specification No 1 186 184 are described in UK Patent Specification Nos 1 431 887 and 1 431 888 (corresponding to U.S. Pat. No. 3,884,926).

The adjustment of pH in step (ii) may suitably be carried out by means of an appropriate buffer solution. The pH is preferably adjusted to a pH between 8.3 and 8.6 since the separation of Factor VIII in step (iii) has been found to be most sharply defined when the pH of the migrant solution is within this range. A further preferment is that the electrical conductivity of the migrant solution is 1.0 mScm$^{-1}$ or less, for example in the range 0.75 to 1.0 mScm$^{-1}$, where all conductivity values are as measured at 20° C.

Step (iv) may be carried out as described in the above mentioned UK Patent Specification Nos. 1 431 887 and 1 431 888. Thus, if the method of the invention is carried out as described in these specifications, the direction of migration of the migrant solution is centrifugal and the injection thereof accordingly effected at the inner side of the flow of the carrier solution. The direction of flow is generally upward and is helical in pattern because of the effect of the rotation of the rotor. Separated components may then be collected by means of an off-take system located in the stator and consisting of a series of parallel mazeplates with spacers. A particular separated component may then pass through one or more particular mazeplates and hence into collecting tube(s).

The final product of the method of the invention may be too dilute for practical purposes. Concentration may therefore be carried out by methods known in the art, for example by ultrafiltration or by precipitation using polyethylene glycol. The final product may also contain lipids which would block filters and make the product difficult to administer if not removed. Removal is therefore highly desirable and may be effected by centrifuging to remove lipid as a surface layer, followed by filtration. Care must, however, be taken to ensure that the Factor VIII remains in solution.

One way of carrying out the invention is described in detail below by way of example only. Reference will be made to the accompanying drawing, the sole FIGURE of which shows the distribution of Factor VIII and of protein among the outlet ports of the apparatus used below and after carrying out steps (i) to (iv) below.

EXAMPLE

Step (i)

Fresh frozen blood plasma was thawed rapidly in a water-bath at 37° C., the pH adjusted to 7.0 by means of 0.1 M citric acid and then cooled to 0° C. 95% ethanol was carefully added so that the temperature of the plasma was maintained at 0° C. and until the ethanol constituted 25% (volume/volume) of the liquid. A precipitate was allowed to develop for 30 minutes whilst the temperature dropped to −5° C.

Step (ii)

The above precipitate was removed by centrifugation at 5000 g for 15 minutes at −5° C. and was then redissolved in an aqueous tris-citrate solution of half the strength of the carrier solution referred to in step (iii) below adjusted to pH 7.5. The solution was assayed and found to contain 80 to 90% of the Factor VIII procoagulant activity of the original plasma, together with all the immunoglobulin, fibrinogen and lipid content of the original plasma; however, half the protein content (largely albumin) was contained in the supernatant liquid. The assay procedure used was as described in American Journal of Chemical Pathology, Vol 61 No. 2, February 1974; "Reassessment of a Non-Haemophilic Reagent for Factor VIII (AHF) Determination" by de Angula & Frommel. The pH of the solution was adjusted to 8.5 immediately before carrying out step (iii) below.

Step (iii)

The above solution, as a migrant solution, was warmed to 20° C. and electrophoresed using a continuous electrophoretic separation apparatus of the type generally described in UK Patent Specification Nos. 1 431 887 and 1 431 888. The apparatus had 29 outlet ports, a stator radius of 40 mm, a rotor radius of 45 mm to give an annular gap of 5 mm, and electrodes 304 mm in length. A carrier solution at 2° C. comprising an aqueous tris-citrate solution (pH 8.5 electrical conductivity 1 mScm$^{-1}$ at 20° C.) was passed upwardly through the annular gap at a rate of 500 ml/minute and the flow stabilised by rotation of the rotor. The migrant solution was injected into the annular gap at a rate of 10 ml/minute. The electrophoresis was carried out at 35 amps and 30 volts giving a temperature rise of carrier solution of 21° C., i.e., from 2° C. to 23° C. The electrolytes were ammonium acetate (1 M; pH 7.5) for the cathode and an equal volume mixture (pH 7.5) of ammonium citrate (0.2 M) and ammonium phosphate (0.15 M) for the anode.

Step (iv)

Fractions were collected from the individual outlet ports of the apparatus and the pH adjusted to be within the range of 7 to 7.5 immediately after collection. The products from individual outlet ports were assayed for Factor VIII and for protein. The results are summarised in the accompanying drawing wherein the continuous line represents protein concentration and the line linked by filled circles the Factor VIII concentration. The circles themselves represent invidual values. The results show that the Factor VIII peak is sharp and that almost all of the Factor VIII is contained in the products of 4 to 5 outlet ports. The results also show that the major part of the protein is separated from the Factor VIII.

The percentage recovery of the Factor VIII and its purity clearly depend upon the number of fractions (i.e. products from individual outlet ports) that are combined to constitute the final product. In this example, 70% of the Factor VIII procoagulant activity (compared with the product of step (i)) was recovered in the four fractions defining the peak in the accompanying drawing. Thus the recovery for the whole process was about 60%. The fractions obtained are diluted approximately ten fold with respect to the initial plasma. Total recovery appears to be substantially the same at migrant solution pH's within the range of 7.5 to 8.5 but the recovery of Factor VIII in the above four fractions was lower at lower pH's, i.e. the Factor VIII peak in the accompanying drawing would be broader at lower pH's.

If necessary, the following additional steps of concentration and/or lipid removal may be carried out on the product of step (iv).

1. Concentration

Concentration is important in order to produce a Factor VIII product suitable for use. This was carried out by the following alternative methods in specific cases.

(a) Ultrafiltration

A pooled fraction of 4 peak fractions from step (iv) was ultrafiltered to 1/10th volume using an Amicon CH3 hollow fibre concentrators with a 10000 molecular weight cut off and freeze dried. After re-dissolving, it was found that 70% of the original Factor VIII activity remained.

(b) Precipitation

A pooled fraction of 4 peak fractions from step (iv) was cooled to 4° C. and solid polyethylene glycol (PEG 6000) added to a final concentration of 7.5% (weight per volume). The PEG 6000 was allowed to dissolve over 1 hour and the resulting precipitate removed by centrifugation (5000 g; 30 minutes) and redissolved in a tris-citrate buffer (1/20th of the volume of the original plasma). The solution was turbid at this stage due to the presence of large amounts of lipids. Recovery of Factor VIII activity was measured and found to be 90–100%.

2. Lipid Removal

A pooled fraction as above was treated with sodium chloride (up to 0.5 M) and the lipid removed by centrifugation. In this way, 80% of the Factor VIII was removed from the lipid.

We claim:

1. In a method of purifying an initial Factor VIII containing aqueous solution which comprises subjecting a Factor VIII containing aqueous migrant solution to continuous flow electrophoresis by injecting the solution into a second aqueous solution, laminarly flowing in an annular separation chamber as a carrier solution for the migrant solution and stabilised by means of an angular velocity gradient, and applying a constant electric field across the resulting mixture to produce a differential movement of the Factor VIII component of the migrant solution with respect to the other major components of the solution perpendicular to the direction of flow of the layer; and collecting the separated Factor VIII component, the improvement wherein the migrant solution is prepared by (i) contacting the initial Factor VIII containing aqueous solution with ethanol under conditions to precipitate Factor VIII; and (ii) removing and redissolving the precipitation in an aqueous medium and adjusting the pH to be within the range of 7.5 to 8.6.

2. A method as claimed in claim 1 wherein, the step (ii), the pH is adjusted to a pH between 8.3 and 8.6.

3. A method as claimed in claim 1 wherein the initial Factor VIII containing solution is in the form of blood plasma.

* * * * *